United States Patent
Stewart (10) Patent No.: US 6,742,894 B2
(45) Date of Patent: Jun. 1, 2004

(54) SYSTEM AND METHOD FOR FULL FIELD OSCILLATING STIMULUS PERIMETER

(75) Inventor: Jeffrey L. Stewart, Greenwich, CT (US)

(73) Assignee: VisionRx, Inc., White Plains, NY (US)

( * ) Notice: Subject to any disclaimer, the term of this patent is extended or adjusted under 35 U.S.C. 154(b) by 0 days.

(21) Appl. No.: 09/968,203

(22) Filed: Oct. 1, 2001

(65) Prior Publication Data

US 2003/0081176 A1 May 1, 2003

(51) Int. Cl.[7] ............................................... A61B 3/02
(52) U.S. Cl. ........................................................ 351/237
(58) Field of Search .................................. 351/222, 239, 351/242, 243, 246, 232, 200, 201, 202; 600/558

(56) References Cited

U.S. PATENT DOCUMENTS 4,256,368 A * 3/1981 Task ............................ 351/239
6,045,515 A * 4/2000 Lawton ....................... 600/558
6,213,956 B1 * 4/2001 Lawton ....................... 600/558

* cited by examiner

Primary Examiner—George Manuel
(74) Attorney, Agent, or Firm—John De La Rosa (57) ABSTRACT

A novel visual field test utilizing oscillating visual stimuli is proposed, which may be used to diagnose for eye disorders, such as glaucoma or macular degeneration. Such visual stimuli oscillate in color, polarity, saturation, luminance or intensity. Preferably, the visual test pattern consists of oscillating visual stimuli arranged in a pattern, such as a repeating or grid pattern, covering substantially all of the field of vision being tested. And, may include the use of frequency doubling visual stimuli. In use, the visual field test pattern is positioned in front of the patient so as to cover substantially all of the field of vision being tested, typically about a solid angle of 40° or more. The eye under examination is fixated, and the patient asked to indicate areas where the oscillating visual stimuli are dissimilar, such as by outlining those areas different from the rest of the visual field test pattern. This procedure may be repeated for different contrast, saturation, or luminance levels, corresponding to varying degrees of visual sensitivity levels. Areas of dissimilarity correspond to visual field defects. The characteristic locations of the areas of dissimilarity for a particular sensitivity setting will allow clinicians not only to diagnose, but also to determine the severity of the eye disorder.

50 Claims, 6 Drawing Sheets

SYSTEM AND METHOD FOR FULL FIELD OSCILLATING STIMULUS PERIMETER

TECHNICAL FIELD

The present invention relates to a visual test system and method for testing the functioning of different parts of the retina and other potions of the visual pathway.

BACKGROUND OF THE INVENTION

A large number of degenerative eye disorders, such as glaucoma and macular degeneration, may be detected by evaluating a patient's visual field, such as through perimetry and campimetry. While the patient's eye is fixated, such visual tests present discrete light stimuli in the patient's field of vision, and then monitor the patient's response to the stimuli, allowing a mapping of the visual field to be obtained.

Visual field tests employing test patterns have also been developed for measuring a patient's visual field. One such visual test uses a so-called "Amsler grid" consisting of equally spaced, parallel, horizontal and vertical lines. In use, the grid is positioned about 28–30 cm in front of the patient. With one eye covered, the other eye is fixated on a central point positioned in the grid, such as a dot. The patient is then asked to indicate areas of distortion in the grid by, for example, drawing an outline around the areas of grid distortion, such as, missing squares or wavy lines. Over time, the patient is again asked to note any changes that occur in the severity or location of the grid distortion, typically on a daily or weekly basis.

Visual field tests employing discreet light stimuli, shown one at a time, have been in use and afford accurate thresholding to determine quantitatively the loss of the patient's visual field. However, such visual tests are very time consuming as well as fatiguing in nature, often requiring the patient to keep his eye fixated for more than 10 minutes. While visual tests employing an Amsler grid are much quicker, thus reducing fatigue, they are generally unable to determine quantitatively the loss of the patient's visual field.

Recently, a computer-based Amsler grid test has been developed for providing a 3-D depiction of a patient's visual field. See the press release at www.wfbabcom5.com/wf335.htlm entitled "3-D Computer-Based Threshold Amsler Grid Test." The computerized test displays an Amsler grid at a pre-selected grayscale level and angular resolution on a computer screen positioned a fixed distance from the patient. The patient is then asked to mark areas on the Amsler grid that are missing from his field of vision. This same procedure is then repeated at various contrast levels. The recorded results are then used to display the areas of distortion (X and Y axes) as a function of the visual contrast sensitivity (Z axis). Ostensibly, such a visual field mapping describes the location, extent, slope, depth and shape of the scotomas associated with the loss in the patient's visual field.

Although no drawbacks are known to the above computerized Amsler grid test, it would still be desirable to have another visual field test which may be capable of more quantitatively, and with greater sensitivity determining a patient's visual field.

SUMMARY OF THE INVENTION

A novel visual field test utilizing oscillating visual stimuli is proposed, which may be used to diagnose for degenerative eye disorders, such as glaucoma or macular degeneration. Such visual stimuli oscillate in color, polarity, saturation, luminance or intensity. Preferably, the visual test pattern consists of oscillating visual stimuli arranged in a pattern, such as a repeating or grid pattern, covering substantially all of the field of vision being tested. Also, frequency doubling visual stimuli may be used, and if desired, the visual stimuli can be caused to move slowly within the patient's central field of view.

In use, the visual field test pattern is positioned in front of the patient so as to cover substantially all of the field of vision being tested, typically a solid angle of 40° or more. The eye under examination is fixated, and the patient asked to indicate areas where the oscillating visual stimuli are dissimilar, such as by outlining those areas different from the rest. This procedure may be repeated for different contrast, saturation or luminance levels, corresponding to varying degrees of visual sensitivity levels. Areas of dissimilarity correspond to visual field defects. The characteristic locations of the areas of dissimilarity for a particular sensitivity setting will allow clinicians not only to diagnose, but also to determine the severity of the eye disorder.

In one embodiment, the visual field test pattern consists of oscillating visual stimuli arranged in a grid pattern. The visual stimuli are located along equally spaced, parallel, horizontal and vertical lines, with a grid spacing of about 1–2 arc minutes. Each visual stimulus has alternating complementary or counter-phase colors oscillating between two complementary or counter phase colors at a frequency $f_s$ of about 10–50 Hz.

In another embodiment, the visual field test pattern consists of visual stimuli arranged in a similar grid pattern, but oscillating in polarity between black and white at a frequency of about 10–50 Hz. As above, the eye under examination is fixated, and the patient asked to indicate areas where the visual stimuli for a pre-selected contrast level are dissimilar, such as appearing more gray or unobservable. Alternatively, the visual stimuli can oscillate between intensity levels.

In still another embodiment, the visual field test pattern consists of color frequency doubling visual stimuli similarly arranged in a grid pattern. Each visual stimulus consists of a circular grating pattern having oscillating colors, shown to produce the frequency doubling phenomenon. Although the luminance level remains constant, the color of each grating oscillates preferably between two colors at a frequency $f_s$ of about 10–50 times a sec. Alternatively, the visual stimuli can oscillate between saturation or luminance levels.

In another embodiment, the visual field test pattern can consist of a sinusoidal grating pattern having horizontal light and dark bars, contrast modulated at a temporal frequency between 10 and 50 Hz. That is, the bars are contrast modulated in a sinusoidal fashion from white through gray to black at about 10 to 50 times a sec. At such frequencies, the grating pattern is perceived by patients to have double the spatial frequency.

In another embodiment, the light and dark bars can be oriented vertically, instead of horizontally. Furthermore, the grating pattern can be caused to move slowly in a direction at right angles to the lengthwise direction of the grating pattern. In this latter instance, patients would then be asked to identify areas of the visual field test pattern where they fail to observe the direction of movement of the pattern.

Still further, the sinusoidal grating pattern may be alternated between horizontal and vertical, or any two directions. And, the grating pattern need not be contrast modulated in a sinusoidal fashion, but may simply oscillate in polarity between black and white, for example using oscillating dots. Alternatively, a checkerboard pattern oscillating in polarity can also be used.

BRIEF DESCRIPTION OF THE DRAWINGS

The features and advantages of the present invention will become more readily apparent from the following detailed description of the invention in which like elements are labeled similarly and in which.

DETAILED DESCRIPTION

In accordance with the principles of the invention, a novel visual field test utilizing oscillating visual stimuli is proposed, which may be used to diagnose for degenerative eye disorders, such as glaucoma or macular degeneration. The visual stimuli oscillate temporally in color, polarity, saturation, luminance or intensity. The visual test pattern consists of one or more oscillating visual stimuli which may be arranged, for example, in a repeating or grid pattern, and, may include the use of frequency doubling visual stimuli.

In use, the visual field test pattern is positioned in front of the patient so as to cover substantially all of the field of vision being tested, typically a solid angle of about 40° or more. The eye under examination is fixated, and the patient then asked to indicate areas where the oscillating visual stimuli are dissimilar, such as by outlining those areas different from the rest of the visual field test pattern. This procedure may be repeated for different contrast, saturation, or luminance levels, corresponding to varying degrees of visual sensitivity levels. Areas of dissimilarity correspond to visual field defects. The characteristic locations of the areas of dissimilarity for a particular sensitivity setting should allow clinicians not only to diagnose, but also to determine the severity of the eye disorder.

Figure 1:
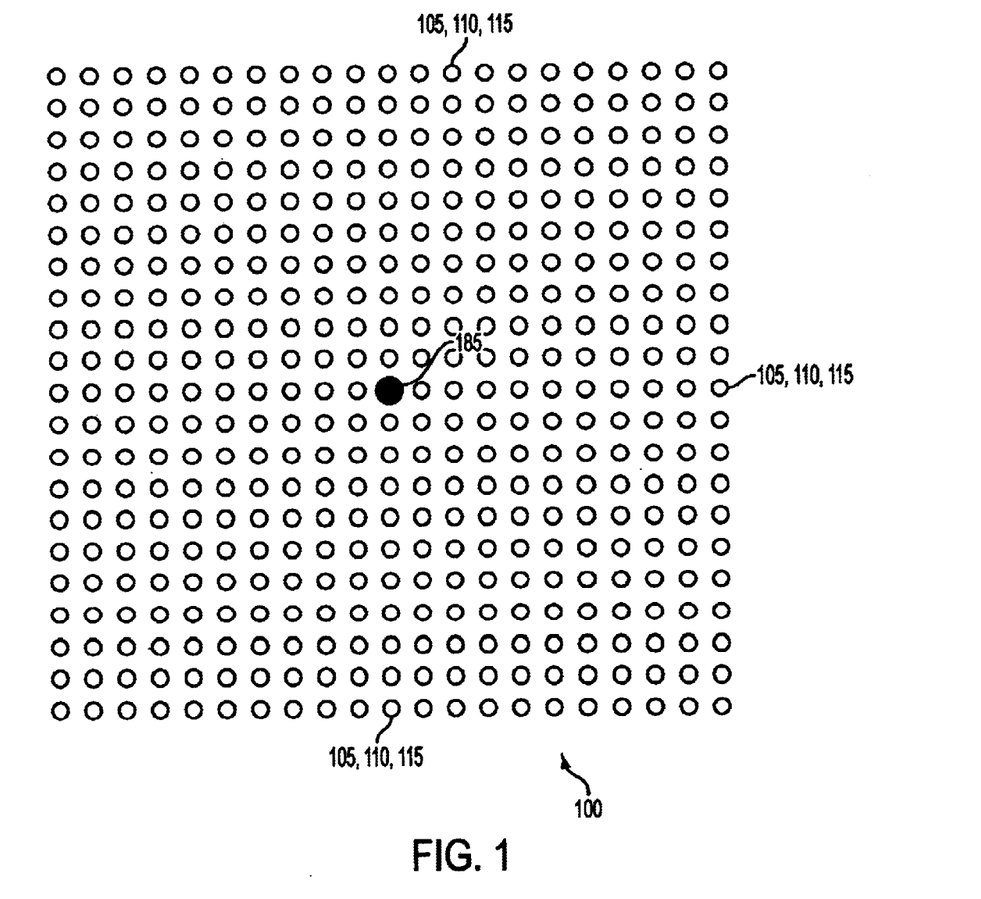
FIG. 1 depicts one embodiment of a visual field test pattern consisting of oscillating visual stimuli arranged in a grid pattern in accordance with the principles of the present invention.

Referring to FIG. 1, there is shown one embodiment of a visual field test pattern 100 consisting of oscillating visual stimuli 105 arranged, for example, in a grid pattern.

Figure 2:
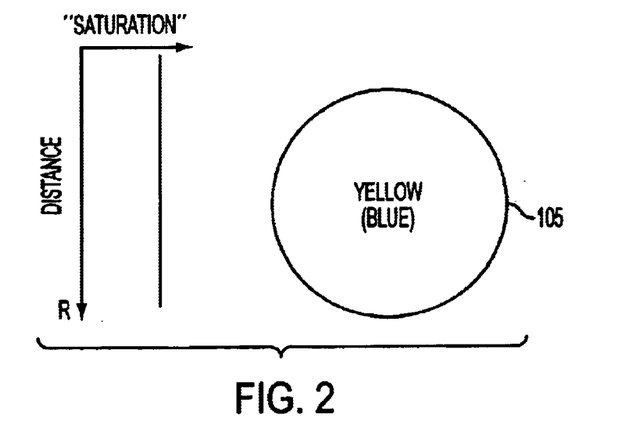
FIG. 2 depicts a color visual stimulus having alternating complementary or counter-phase colors.

Alternatively, the visual stimuli may be randomly spaced or arranged in a circular grid. Preferably, however, visual stimuli 105 are located along equally spaced, parallel, horizontal and vertical lines. The grid spacing is about 1–2 arc minutes. Each visual stimulus 105 has alternating complementary or counter-phase colors (chromatic stimulus). See U.S. Pat. No. 6,227,668, which is incorporated herein by reference. As shown in FIG. 2, each visual stimulus 105 oscillates between the two complementary or counter phase colors at a frequency $f_s$ of about 10–50 Hz, preferably 40 Hz. In other words, each visual stimulus switches back and forth between the two colors at the desired frequency, here the complementary color pair of blue and yellow.

The "saturation" or "purity" of each color throughout visual stimulus 105 is substantially uniform. Throughout this specification, the term saturation S or purity refers to the amount of dilution of the pure color or hue with neutral gray of the same luminance, as commonly used in the field of colorimetry. The saturation S varies from 0 to 1, and has a maximum purity at S=1. In some chromaticity diagrams or color systems, this latter characteristic of color is known as chroma.

When the colors in visual stimulus 105 are oscillated at a frequency between 10–50 Hz, it appears white (or gray) to the observer, instead of either blue or yellow. With one or both eyes open, the eye(s) under examination is fixated, and the patient asked to indicate areas where visual stimuli 105 for a pre-selected saturation level in visual field test pattern 100 appear dissimilar, either appearing more gray or unobservable. Areas of dissimilarity correspond to visual field defects within the retina's visual field.

The above procedure may be repeated for different color saturation levels to establish the eye's sensitivity level. Recall that as the saturation is reduced from its maximum (S=1), each visual stimulus appears to get grayer, and then eventually cannot be perceived. Mapping the areas of dissimilarity as the color saturation is reduced, affords a quantitative measurement of the relative severity of the visual defects.

Alternatively, the above procedure may be repeated for different luminance L levels, while the saturation is held constant. As the luminance is reduced, each visual stimulus appears to get grayer, and then eventually cannot be perceived. Mapping the areas of dissimilarity in visual test pattern as the luminance is reduced, also affords a quantitative measurement of the relative severity of the visual defects.

In another alternative embodiment, the visual field test pattern consists of one or more color visual stimuli, each of which oscillate between saturation, luminance or intensity levels. In other words, each visual stimulus is of a single color, such as yellow, but switches back and forth between the two pre-selected, intensity, saturation or luminance levels at a desired frequency. Again, the patient is asked to indicate areas where visual stimuli appear dissimilar. Areas of dissimilarity correspond to visual field defects within the retina's visual field. The above procedure may be repeated as the difference between two pre-selected saturation, luminance, or intensity levels is reduced.

Figure 3:
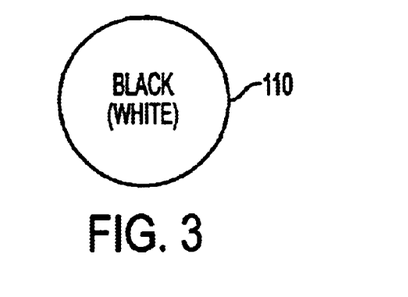
FIG. 3 depicts a visual stimulus consisting of a circular object which is oscillated in polarity between black and white.

In another embodiment of the invention, visual field test pattern 100 consist of visual stimuli 110 arranged in a similar grid pattern, but oscillating in polarity between black and white at a frequency of about 10–50 Hz, as depicted in FIG. 3. Again, the eye under examination is fixated, and the patient asked to indicate areas where visual stimuli 110 for a pre-selected contrast level are dissimilar, such as appearing more gray or unobservable. Areas of dissimilarity correspond to visual field defects within the patient's visual field. Repeating the above procedure for different contrast levels affords a quantitative measurement of the relative severity of the defects.

Figure 4:
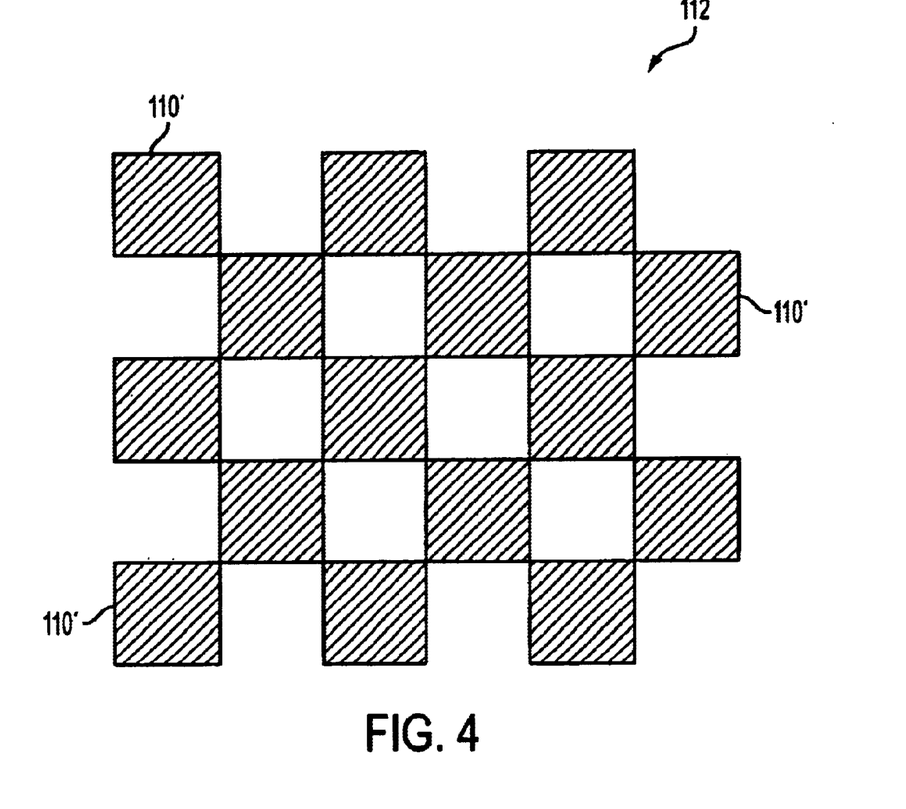
FIG. 4 depicts another embodiment of a visual field test pattern consisting of oscillating visual stimuli arranged in a checkerboard pattern.

Although the above visual stimuli have been depicted as circular, it should be understood that other geometrical shapes can be used, such as squares and triangles. The form of the stimulus is not critical. Although the stimuli are located in a rectilinear grid, it should be understood that other arrangements may be used, including a circular grid, other patterns, or a random distribution of the stimuli. The pattern is not critical so long as they are uniformly distributed across the visual field. For example, square visual stimuli 110' may be employed which are arranged in a checkerboard pattern 112, as depicted in FIG. 4. Similarly, visual stimuli 110' oscillate in polarity between black and white, and substantially cover the retina's central visual field. Additionally, the visual stimuli can be caused to move slowly within the patient's central field of view.

In another embodiment of the invention, a visual field test pattern consisting of color frequency doubling visual stimuli 115 similarly arranged in a grid pattern is proposed. As shown in FIG. 5, each visual stimulus 115 consists of a circular sinusoidal grating pattern having oscillating colors, previously shown to produce a frequency doubling phenomenon. See U.S. Pat. No. 6,068,377, which is incorporated herein by reference. Each visual stimulus 115 consists of a circular grating, here having two spatial cycles (rings 120, and 125). Of course, a linear grating may also be used. Although the luminance level remains constant, the color of each grating oscillates preferably between two colors at a frequency $f_s$ of about 10–50 times a sec, preferably 40 Hz. In other words, each grating synchronously switches back and forth between the two colors at the desired frequency, here the complementary color pair of blue and yellow. Again, the visual stimuli need not be arranged in a rectilinear grid.

Figure 5A:
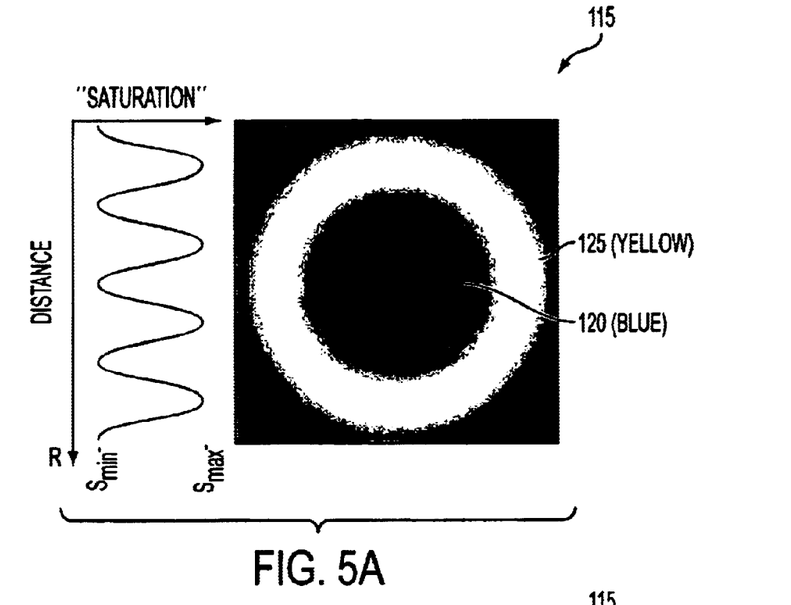
FIG. 5 depicts a frequency doubling visual stimulus consisting of circular color grating, one blue and one yellow which when oscillated between the two colors is observed as having double the spatial frequency.
Figure 5B:
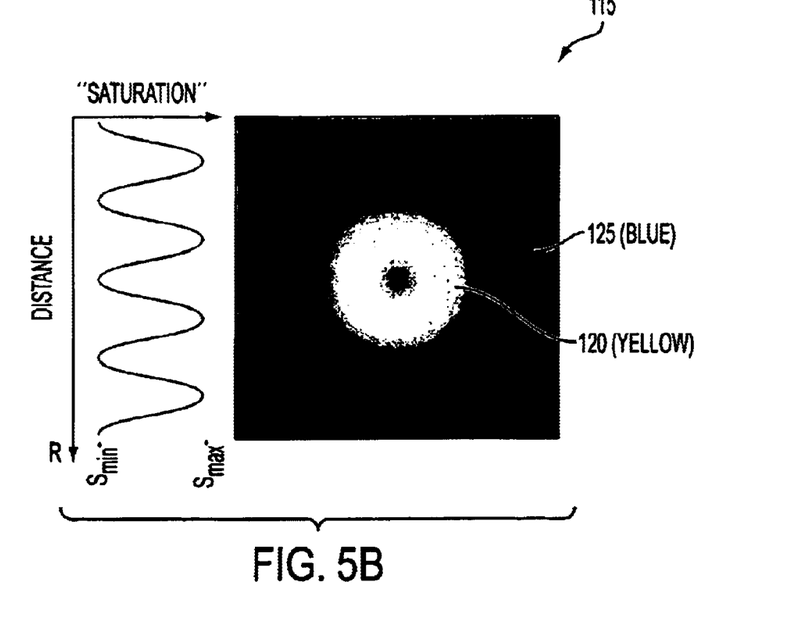

For example, in FIGS. 5(a)–(b), circular ring 120 is first blue then yellow, whereas circular ring 125 is yellow then blue. However, at any instance in time, the "saturation" or "purity" of each color varies sinusoidally in a radial direction, ranging from a maximum to a minimum, as further depicted in the figure. Thus, near the edges of each ring, each color appears pale or gray.

The term "saturation modulation depth" M is defined herein as a functional relationship of the maximum and minimum saturation levels using the equation:

$$M = \frac{(S_{max} - S_{min})}{(S_{max} + S_{min})}$$

where $S_{max}$ is the maximum saturation level and $S_{min}$ is the minimum saturation level. See, for example, FIG. 5.

When the colors in color visual stimulus 115 are alternated at a frequency between 10–50 Hz, a frequency doubling phenomenon causes twice the number of cycles/degrees to be perceived. The eye under examination is fixated, and the patient then asked to indicate areas where color visual stimuli 115 for a pre-selected saturation level or modulation depth appear different, such as by outlining those areas in visual field test pattern 100. Again, areas of dissimilarity correspond to visual field defects, such as a scotoma. This procedure may be repeated for different saturation levels, or modulation depth values, including varying the maximum and minimum saturation level by the same amount for both colors.

Figure 6:
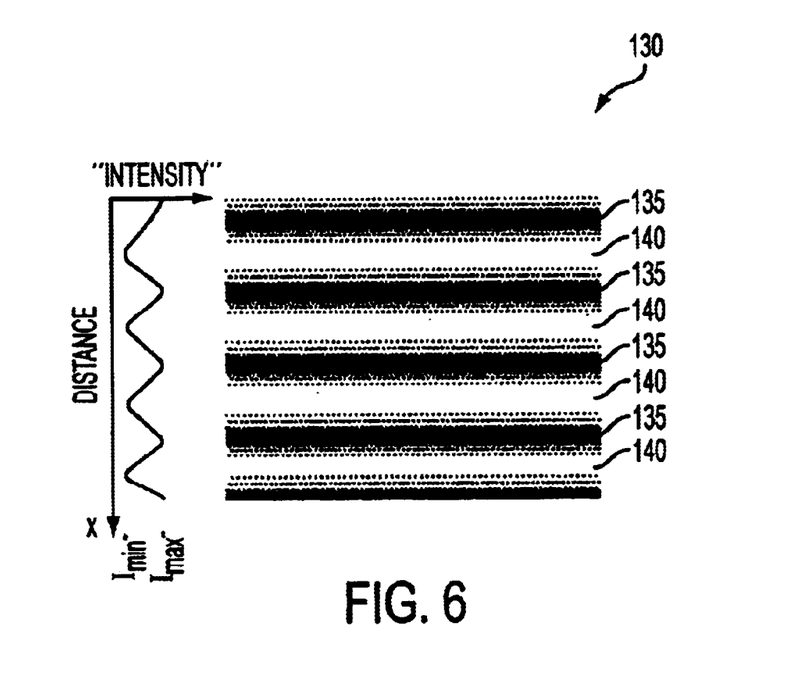
FIG. 6 depicts a visual stimulus consisting of a black and white sinusoidal grating which when oscillated in polarity is observed as having double the spatial frequency.

In still another embodiment of the present invention, a visual field test pattern consisting of a sinusoidal grating pattern is proposed, which grating pattern is presented so as to cover the entire portion of the field of vision of the retina. As shown in FIG. 6, the sinusoidal grating pattern 130 consisting of horizontal light and dark bars 135, 140, respectively, are modulated at a temporal frequency between 10 and 50 Hz. That is, the bars are contrast modulated in a sinusoidal fashion from white through gray to black at about 10 to 50 times a sec. At such frequencies, typically about 40 Hz, the grating pattern is perceived by patients to have double the spatial frequency. For a discussion on this phenomenon, see, for example, D. H. Kelly, "Frequency Doubling In Visual Response," *J. Opt. Soc. Am.*, 56:1628–33 (1966); and D. H. Kelly, "Nonlinear Visual Responses To Flickering Sinusoidal Gratings," *J. Opt. Soc. Am.* 1051–55 (1981).

With visual field test pattern 130 displayed to the patient, the eye under examination is fixated, and the patient then asked to indicate areas where the stimulus appears different for a pre-selected stimulus level. Again, areas of dissimilarity correspond to visual field defects. Similarly, this procedure may be repeated for different contrast levels.

Alternatively, light and dark bars 135, 140 can be oriented vertically, instead of horizontally, or at some other angle. The grating may also be circular, square, or some other shape. Furthermore, the grating pattern can be caused to move slowly in a direction at right angles to the lengthwise direction of the grating pattern. In this latter instance, patients would then be asked to identify areas of the visual field test pattern where they fail to observe the direction of movement of the pattern.

In still another embodiment, the visual field test pattern consists of a sinusoidal grating pattern, as discussed herein above, alternating between horizontal and vertical.

In the above embodiments, the grating pattern need not be contrast modulated in a sinusoidal fashion, but simply oscillate in polarity between black and white, without going through gray. Also, the pattern may be in the form of a checkerboard.

Preferably, the visual field test pattern is viewed from a distance at which it covers a substantial portion of the retina's central field of vision, which can be readily adjusted by judiciously selecting the dimensions of the visual field pattern, as well as the distance from which it is observed.

Figure 7:
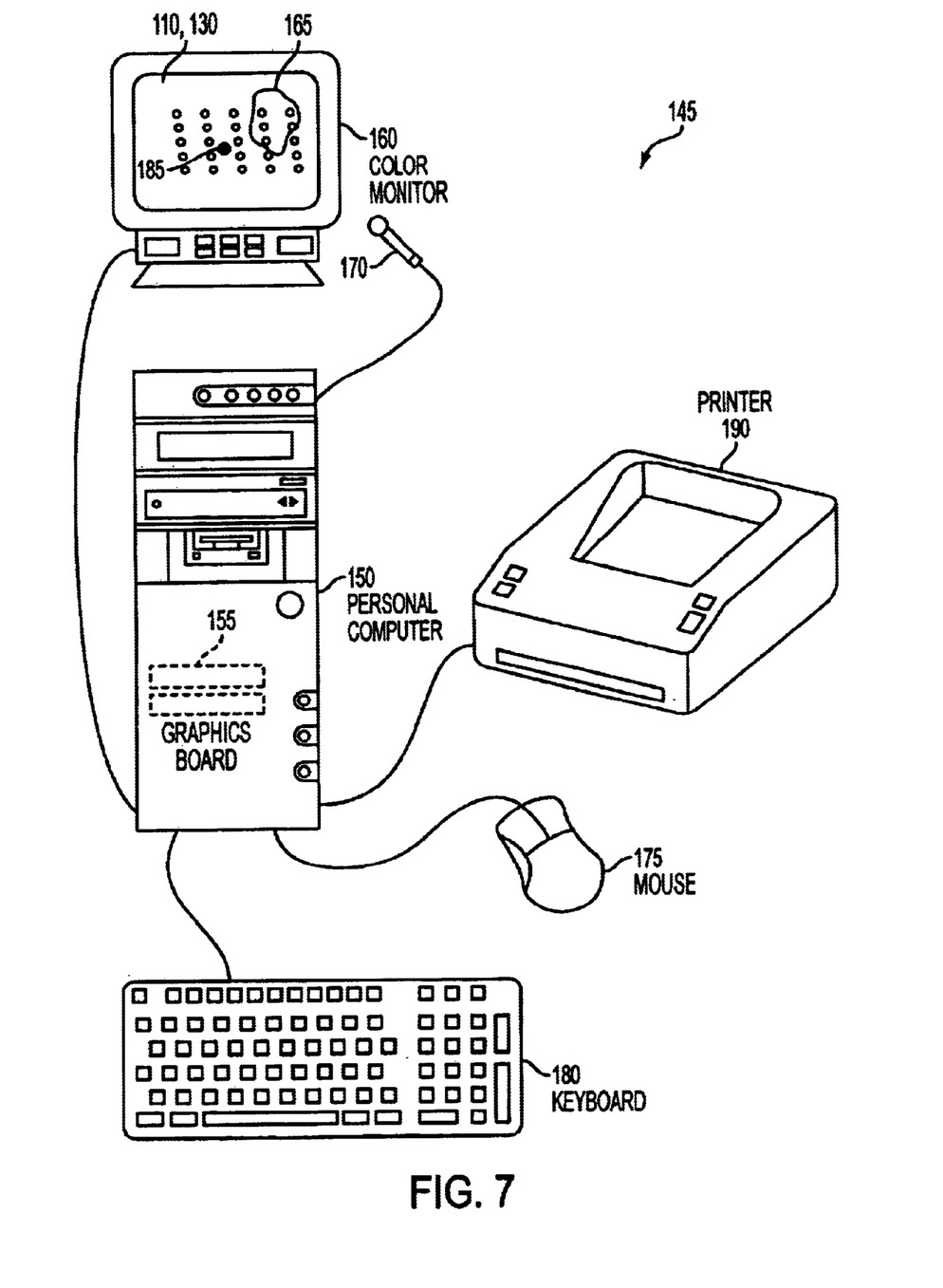
FIG. 7 depicts a simplified block diagram of a visual field test measurement system which may be employed to map a patient's visual field in accordance with the principles of the invention.

Inasmuch as the present invention also encompasses an apparatus for performing the above inventive visual field test measurement, shown in FIG. 7 is a simplified block diagram of a visual field test measurement system 145 in accordance with the principles of the invention. Visual field test measurement system 145 comprises a computer 150, such as a personal computer (PC) running under Windows. Computer 150 includes conventional graphics boards 155 which may be readily programmed to display visual field test pattern 100 or 130 against a desired colored or gray background on a color monitor 160.

Importantly, visual field test pattern 100 or 130 covers the entire portion of the retina's visual field, e.g., about 40° solid angle around center. Recall that the visual field test pattern consists of visual stimuli arranged in a repeating or grid pattern that oscillates in color or polarity, as discussed herein above. The visual stimuli are displayed at a pre-selected contrast, luminance or saturation level. Preferably, visual field test pattern 100 or 130 is about 12 inches wide by 9 inches high, with a viewing distance of about 16 inches. In addition to displaying the visual field test pattern, computer 150 monitors the patient's response thereto, which is entered by outlining areas of dissimilarity 165 within the visual field test pattern using a light pen 170, or alternatively a mouse 175 or joystick, or through the use of a touch screen digitizer or digitizing tablet, among other devices.

In the preferred embodiment, the patient views color monitor 160 at a predetermined distance for the visual field pattern to substantially subtend the entire portion of the retina's visual field being tested. Of course, the patient may view the visual field pattern monocularly, with each eye tested separately. An operator may be seated at or near computer 150 for controlling the test via a keyboard 180, or the testing may be fully automated, or even conducted through the Internet.

The patient's central vision can be fixated, either using a single fixation target 185 or a fixation targets located at several positions. The patient may be asked to move a cursor towards a fixation target which is also displayed on the computer monitor, as disclosed more fully in copending application Ser. No. 09/604,571 entitled "Method For Establishing Fixation In Visual Field Perimetry," which is incorporated herein by reference. Alternatively, the moving fixation technique disclosed in U.S. Pat. No. 5,565,949 may be employed, which is incorporated herein by reference. The fixation target may be located at one place in the center of the visual field test pattern or moved to different locations to increase the area of coverage of the retina. The fixation target may be made with a variety of symbols such as a simple colored dot, an alpha-numeric character or a picture, such as a house or cat.

Once having established fixation, visual field test pattern 100 or 130 is displayed to the patient at a pre-selected contrast, luminance or saturation level. The patient then uses light pen 170 or other input device, to trace an outline of the areas of dissimilarity 165 in the visual field test pattern 100 or 130. The appearance of the areas of dissimilarity may vary, and is dependent on the type of visual stimuli employed and the type of eye disorder present in the patient. If desired, this procedure may be repeated for different contrast, color saturation, or luminance levels, which establishes the eye's sensitivity level, depending on the type of visual stimuli used in the visual field test pattern. Each time the procedure is repeated, the patient's eye is fixated, and the patient asked to denote the areas of dissimilarity in the visual field pattern which correspond to visual field defects. The characteristic locations of the areas of dissimilarity for a particular sensitivity setting should allow clinicians not only to diagnose, but also to determine the severity of the eye disorder.

Software to implement the above described visual field perimetry therefore includes displaying and, if desired, varying the saturation, luminance and/or contrast of the stimuli, monitoring the patient's fixation, recording the patient's response to the visual field pattern, and mapping the visual field on the basis of the patient's responses. Such software is readily capable of implementation by those skilled in the art who have been equipped with the understanding of the operation of the present invention as set forth herein, and may be written in C++, or any other programming language.

In addition to graphically displaying the patient's visual field on the monitor or on a printer 190, the visual field mapping can be saved on hard disk, recalled for later use, imported into a database for statistical analysis, and/or transmitted to a remote location.

Although the present invention has been realized and discussed in terms of displaying the visual field test pattern on color monitor 160, it is to be clearly understood that the present invention may have equally employed other types of displays, such as projection screens, LCDs, heads up displays (HUDs), total immersion displays, and the like. Also, the present invention may employ the multi-functional visual testing instrument of U.S. Pat. No. 6,045,227, which is incorporated herein by reference.

Figure 8:
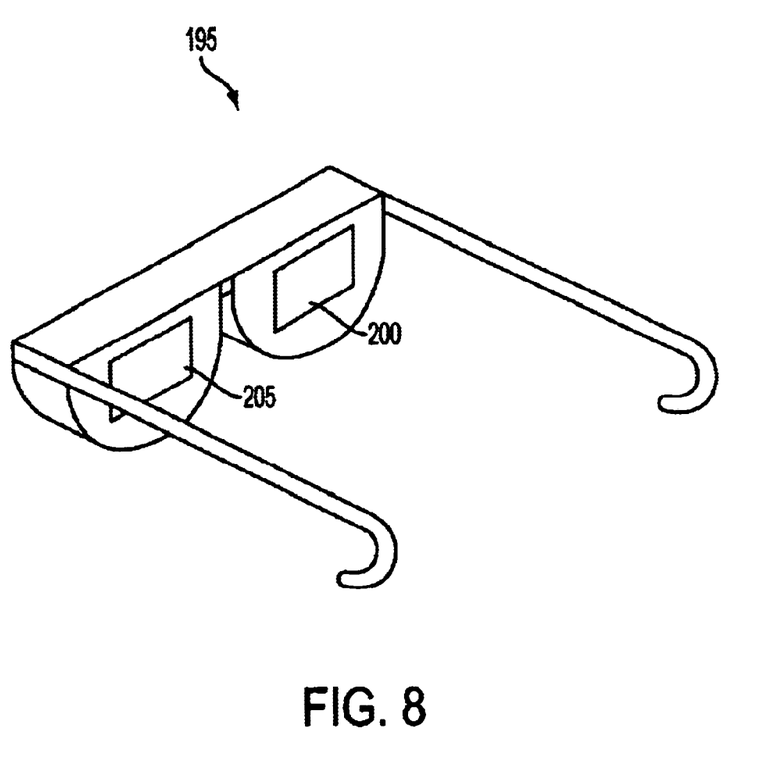
FIG. 8 depicts a close proximity display in the form of a close proximity display, which may be used by a patient to observe the visual field test pattern of FIG. 1.

Still further, as shown in FIG. 8, total immersion displays, such as close proximity displays in the form of virtual reality glasses 195, may be used to display the visual field test pattern to the patient, which advantageously may contain two independent displays 200, 205. See, for example, U.S. Pat. Nos. 5,565,949; and 5,737,060, which are incorporated herein by reference. In this latter case, both eyes can be tested by displaying the visual field test pattern to each eye independently. That is, the visual test field pattern is first displayed to right eye display 200 of virtual reality glasses 195, and then to left eye display 205, without the patient being able to distinguish which eye is being tested. Note that in this latter instance, the patient will view the fixation target binocularly. Similarly, testing may then be performed as discussed herein above.

It should be clearly understood that the embodiments herein are merely illustrative of the principles of the invention. Various modifications may be made by those skilled in the art which will embody the principles of the invention and fall within the spirit and the scope thereof.

What is claimed is:

1. A method for testing a predetermined visual field of a person, comprising the steps of:

displaying to the person a visual field test pattern having one or more oscillating visual stimuli, said visual test pattern subtending an angle substantially covering all of the predetermined visual field being tested; and inputting the areas of dissimilarity in the visual field test pattern indicated by the person.

2. The method of claim 1 wherein the visual stimuli oscillate between two colors.

3. The method of claim 2 wherein the two colors are complementary colors.

4. The method of claim 1 wherein the visual stimuli oscillate in polarity.

5. The method of claim 1 wherein the visual stimuli oscillate between contrast levels.

6. The method of claim 1 wherein the visual stimuli are color visual stimuli oscillating between saturation levels.

7. The method of claim 1 wherein the visual stimuli are color visual stimuli oscillating between luminance levels.

8. The method of claim 1 wherein the visual stimuli oscillate in intensity.

9. The method of claim 1 further comprising the step of determining a person's eye disorder from the characteristic locations of the areas of dissimilarity.

10. The method of claim 1 further comprising the steps of:

varying the saturation, contrast, intensity or luminance level of the visual stimuli;

recording the areas of dissimilarity indicated by the person for a pre-selected saturation, contrast, intensity or luminance level; and diagnosing the severity of the person's eye disorder from the characteristic locations of the areas of dissimilarity for the different levels of saturation, contrast, intensity or luminance.

11. The method of claim 10 further comprising the step of displaying the area of dissimilarity as a function of the saturation, contrast, intensity or luminance level of the visual stimuli.

12. The method of claim 1 wherein the step of indicating areas of dissimilarity includes outlining those areas in the visual field test pattern different from the rest of the visual field test pattern.

13. The method of claim 1 wherein the visual stimuli are arranged in a repeating or grid pattern.

14. The method of claim 13 wherein the grid pattern is defined by equally spaced lines along two directions.

15. The method of claim 1 further including the step of fixating the person's central vision.

16. The method of claim 1 wherein the predetermined field of vision is about a solid angle of 40° or more.

17. The method of claim 1 wherein the visual stimuli are color frequency doubling visual stimuli.

18. The method of claim 17 wherein the color frequency doubling visual stimuli consist of a circular grating pattern having oscillating colors that produce a frequency doubling phenomenon.

19. The method of claim 18 wherein the saturation level of each color varies sinusoidally radially.

20. The method of claim 1 wherein the visual field test pattern consists of a sinusoidal grating pattern of light and dark bars oriented along a first direction.

21. The method of claim 20 further comprising the step of causing the grating pattern to move slowly in a direction at right angles to said first direction.

22. The method of claim 20 further comprising the step of alternating the sinusoidal grating pattern between a first and second orientation.

23. The method of claim 1 further comprising the step of moving the visual field test pattern within the visual field of the person.

24. The method of claim 1 wherein the visual stimuli are arranged in a checkerboard pattern.

25. A system for testing a predetermined visual field of a person, comprising:

a display;

means for displaying to the person a visual field test pattern having one or more oscillating visual stimuli, said visual test pattern subtending an angle substantially covering all of the predetermined visual field being tested; and means for allowing the person to indicate areas of dissimilarity in the visual field test pattern.

26. The system of claim 25 wherein the visual stimuli oscillate between two colors.

27. The system of claim 26 wherein the two colors are complementary colors.

28. The system of claim 25 wherein the visual stimuli oscillate in polarity.

29. The system of claim 25 wherein the visual stimuli oscillate between contrast levels.

30. The system of claim 25 wherein the visual stimuli are color visual stimuli oscillating between saturation levels.

31. The system of claim 25 wherein the visual stimuli are color visual stimuli oscillating between luminance levels.

32. The system of claim 25 wherein the visual stimuli oscillate in intensity.

33. The system of claim 25 wherein the person's eye disorder is determined from the characteristic locations of the areas of dissimilarity.

34. The system of claim 25 further comprising:

means for varying the saturation, contrast, intensity or luminance level of the visual stimuli;

means for recording the areas of dissimilarity indicated by the person for a pre-selected saturation, contrast, intensity or luminance level, and correlating them with a person's eye disorder, with the severity thereof being determined from the characteristic locations of the areas of dissimilarity for the different levels of saturation, contrast, intensity or luminance.

35. The system of claim 25 further comprising means for displaying the area of dissimilarity as a function of the saturation, contrast, intensity or luminance level of the visual stimuli.

36. The system of claim 25 wherein said means for indicating areas of dissimilarity includes a light pen.

37. The system of claim 25 wherein said means for indicating areas of dissimilarity includes a touch screen digitizer.

38. The system of claim 25 wherein said means for indicating areas of dissimilarity includes a digitizing tablet.

39. The system of claim 25 wherein the visual stimuli are arranged in a repeating or grid pattern.

40. The system claim 39 wherein the grid pattern is defined by equally spaced lines along two directions.

41. The system of claim 25 further including means for fixating the person's central vision.

42. The system of claim 25 wherein the predetermined field of vision is about a solid angle of 40° or more.

43. The system of claim 25 wherein the visual stimuli are color frequency doubling visual stimuli.

44. The system of claim 43 wherein the color frequency doubling visual stimuli consist of a circular grating pattern having oscillating colors that produce a frequency doubling phenomenon.

45. The system of claim 44 wherein the saturation level of each color varies sinusoidally radially.

46. The system of claim 25 wherein the visual field test pattern consists of a sinusoidal grating pattern of light and dark bars oriented along a first direction.

47. The system of claim 46 further comprising means for causing the grating pattern to move slowly in a direction at right angles to said first direction.

48. The system of claim 46 further comprising means for alternating the sinusoidal grating pattern between a first and second orientation.

49. The system of claim 25 further comprising means for moving the visual field test pattern within the visual field of the person.

50. The system of claim 25 wherein the visual stimuli are arranged in a checkerboard pattern.

* * * * *